US012708286B2

(12) United States Patent
Martinez-Lozano Sinues et al.

(10) Patent No.: US 12,708,286 B2
(45) Date of Patent: Aug. 18, 2026

(54) METHOD FOR PROCESSING MASS SPECTROMETRY DATA OBTAINED FROM BREATH GAS

(71) Applicant: UNIVERSITÄTS-KINDERSPITAL BEIDER BASEL, Basel (CH)

(72) Inventors: Pablo Martinez-Lozano Sinues, Zürich (CH); Kapil Dev Singh, Zürich (CH)

(73) Assignee: UNIVERSITÄTS-KINDERSPITAL BEIDER BASEL, Basel (CH)

( * ) Notice: Subject to any disclaimer, the term of this patent is extended or adjusted under 35 U.S.C. 154(b) by 306 days.

(21) Appl. No.: 18/578,925

(22) PCT Filed: Jul. 7, 2022

(86) PCT No.: PCT/EP2022/068825
§ 371 (c)(1),
(2) Date: Jan. 12, 2024

(87) PCT Pub. No.: WO2023/285253
PCT Pub. Date: Jan. 19, 2023

(65) Prior Publication Data

US 2024/0324897 A1 Oct. 3, 2024

(30) Foreign Application Priority Data

Jul. 13, 2021 (EP) .................................... 21185400

(51) Int. Cl.
*A61B 5/083* (2006.01)
*A61B 5/00* (2006.01)
(Continued)

(52) U.S. Cl.
CPC ............ *A61B 5/0836* (2013.01); *A61B 5/097* (2013.01); *A61B 5/7246* (2013.01); *A61B 5/7264* (2013.01); *G01N 33/4975* (2024.05)

(58) Field of Classification Search
CPC ..... A61B 5/0836; A61B 5/097; A61B 5/7246; A61B 5/7264; A61B 5/082; G01N 33/4975; G01N 33/497
See application file for complete search history.

(56) References Cited

U.S. PATENT DOCUMENTS 10,568,541 B2 2/2020 Wang et al.
11,103,158 B2 * 8/2021 Von Haimberger ... G16H 50/30
(Continued)

FOREIGN PATENT DOCUMENTS

WO WO-2020160753 A1 * 8/2020 ........... G01N 27/623

OTHER PUBLICATIONS

Exhaled breath compositions under varying respiratory rhythms reflects ventilatory variations: translating breathomics towards respiratory medicine, Pritam Sukul et al. Scientific Reports vol. 10, Article No. 14109 (2020) (Year: 2020).*
(Continued)

*Primary Examiner* — Sean P Dougherty
(74) *Attorney, Agent, or Firm* — Sughrue Mion, PLLC

(57) ABSTRACT

A computer-implemented method for processing mass spectrometry data from breath gas including receiving a time-dependent ion profile originating from a spectrometer data sample (D1,D2), the spectrometer data sample (D1,D2) having been recorded during at least one exhalation from a subject (1); each time-dependent ion profile being associated with one mass-to-charge ratio value and including a signal strength for the one mass-to-charge ratio value measured over a time duration. The method further includes receiving a time-dependent breath profile, the time-dependent breath profile having been recorded during the at least one exhalation over the time duration, and a temporal correlation step (200), the temporal correlation step (200) including: determining a degree of temporal correlation between the at least
(Continued)

one time-dependent ion profile and the time-dependent breath profile, and classifying the at least one time-dependent ion profile based on the degree of temporal correlation.

14 Claims, 8 Drawing Sheets

(51) Int. Cl.
*A61B 5/097* (2006.01)
*G01N 33/497* (2006.01)

(56) References Cited

U.S. PATENT DOCUMENTS

| | | | | |
|---|---|---|---|---|
| 2003/0116705 | A1* | 6/2003 | Kanik | A61B 5/083 250/287 |
| 2005/0085740 | A1* | 4/2005 | Davis | G01N 33/497 422/84 |
| 2007/0081162 | A1* | 4/2007 | Roller | G01N 33/497 356/437 |
| 2017/0299477 | A1* | 10/2017 | Milton | G01N 33/497 |
| 2018/0246036 | A1* | 8/2018 | Carty | A61B 5/082 |

OTHER PUBLICATIONS

Kapil Dev Singh et al., "Standardization procedures for real-time breath analysis by secondary electrospray ionization high-resolution mass spectrometry", Analytical and Bionanlytical Chemistry, Apr. 15, 2019, vol. 411, No. 19, pp. 4883-4898.

Yoav Benjamini et al., "Controlling the False Discovery Rate: A Practical and Powerful Approach to Multiple Testing", Journal of the Royal Statistical Society. Series B (Methodological), 1995, vol. 57, No. 1, pp. 289-300.

Colin A. Smith et al., "XCMS: Processing Mass Spectrometry Data for Metabolite Profiling Using Nonlinear Peak Alignment, Matching, and Identification", Analytical Chemistry, Feb. 1, 2006, vol. 78, No. 3, pp. 779-787.

Ralf Tautenhanhn et al., "Highly sensitive feature detection for high resolution LC/MS", BMC Bioinformatics, Nov. 28, 2008, 16pages.

H. Paul Benton et al., "Correction of mass calibration gaps in liquid chromatography-mass spectrometry metabolomics data", Bioinformatics, 2010, vol. 26, No. 19, pp. 2488-2489.

International Search Report for PCT/EP2022/068825 dated Oct. 20, 2022 (PCT/ISA/210).

Written Opinion for PCT/EP2022/068825 dated Oct. 20, 2022 (PCT/ISA/237).

* cited by examiner 1
subject
2
6
3 ionizer
4 mass spectrometer
Z2
Z1
time-dependent total ion profile
spectrometer data samples
D2
D1
11
100
spectral feature extraction
temporal correlation
200
300
integration
400
normalization
10
L2
L1
feature lists
500
filtering
F
final data matrix 14th iteration 0.18
0.16
0.14
0.12
0.10
0.08
0.06
0.04
0.02
0 relative bin counts $f_K$

B 143.02
143.04
143.06
143.08
143.1
143.12
143.14
143.16 m/z

200
$CO_2$ %
$C_1$
time
signal strength
$X_{11}$
time
signal strength
$X_{12}$
time
$T_1$
discard $X_{11}$
$\rho_{11} \geq \rho_{th}$ and $r_{11} \leq r_{th}$?
NO
$\rho_{12} \geq \rho_{th}$ and $r_{12} \leq r_{th}$?
YES
300
$CO_2$ %
$C_2$
time
signal strength
$X_{21}$
time
signal strength
$X_{22}$
time
$T_2$
$\rho_{21} \geq \rho_{th}$ and $r_{21} \leq r_{th}$?
YES
300
$\rho_{22} \geq \rho_{th}$ and $r_{22} \leq r_{th}$?
YES
300

METHOD FOR PROCESSING MASS SPECTROMETRY DATA OBTAINED FROM BREATH GAS

CROSS REFERENCE TO RELATED APPLICATIONS

This application is a National Stage of International Application No. PCT/EP2022/068825 filed Jul. 7, 2022, claiming priority based on European Patent Application No. 21185400.5 filed Jul. 13, 2021.

TECHNICAL FIELD

The present invention relates to a computer-implemented method and a computer program product for processing mass spectrometry data obtained from a breath gas.

PRIOR ART

Breath analysis is a fast-growing field that is concerned with identifying compounds in breath that are produced by metabolic process occurring in the body. Due to its non-invasive nature, breath analysis holds great promises as a patient-friendly diagnosis method for detecting diseases or for monitoring therapeutic efforts. However, linking the occurrence of certain compounds to a specific disease is far from being straight-forward. Breath metabolomics based on mass spectrometry deals with the recognition of compound-patterns and their association with the health state of a patient. Instead of measuring the concentrations of a few known target substances, broad mass spectra may be acquired and analyzed to determine potentially complex spectral "fingerprints" that may be indicative of a particular disease. Since these "fingerprints" are a priori unknown, being able to distinguish between signals originating from the subject's breath and signals originating from unwanted contamination is particularly crucial. Such contamination compounds may enter the mass spectrometer apparatus with the environmental air or may originate from an outgassing process within the apparatus itself.

Although the contamination level may already be significantly reduced by establishing hardware cleaning protocols and ensuring that the measurements are performed in a well-controlled clinical laboratory environment with appropriately filtered environmental air, a post-processing of the raw data is still necessary to obtain reliable and meaningful results.

Performing so-called "real-time" analysis of breath metabolites using mass spectrometry implies that the data acquisition is running while the patient is breathing into the mass spectrometry device, i.e. the breath sample is not stored and cannot be re-measured at a later time.

Obtaining meaningful results when performing such a real-time analysis therefore entails solving two main challenges: temporally selecting the correct data portions that indeed correspond to exhaled breath and spectrally dismissing the features in these data portions that originate from contaminations.

Ideally, the temporal selection also enables the identification of the different phases of the exhalation process and thus enables for instance the distinction between air coming from the upper airways and air coming from the alveoli.

WO2020/160753A1 discloses a set of sensor probes that measure at least one of the following parameters: manometric pressure of the exhalation, exhaled flow rate, exhaled volume, exhaled carbon dioxide ($CO_2$) concentration, exhaled humidity or absolute pressure during the exhalation, while allowing a fraction of the exhaled flow to be passed to a mass spectrometry analyzer. The document discloses a method comprising the steps of synchronizing the data produced by the set of sensor probes with the data produced by the mass spectrometry analyzer, defining a lung fraction by defining thresholds, identifying a time interval for which the data produced by the set of sensors is above, below or within said thresholds and calculating the signal corresponding to said lung fraction as the averaged signal produced by the mass spectrometry analyzer over said time interval.

While the document provides a solution for selecting a desired temporal portion of the breath signal, it is silent about how to dismiss spectral features originating from contaminations that may occur within these desired temporal portions.

U.S. Ser. No. 10/568,541B2 discloses a breath analysis system comprising a gas chromatograph coupled to a detector array and a method of using said system for detecting whether a subject has a respiratory disease or monitoring a subject with a respiratory disease, wherein the method comprises determining a baseline concentration level of both background nitric oxide content and background volatile organic compound content in the ambient air, saving the baseline concentration level and producing an indicator being indicative of one or more biomarkers in the exhaled breath by subtracting the baseline concentration level from output data associated with breath from said subject.

Such a baseline subtraction method however does not take into account the issue of recognizing transient contaminations, i.e. contaminations which may have entered the system while the breath acquisition was running, but may not have been present at the time where the baseline concentration was determined.

SUMMARY OF THE INVENTION

In a first aspect, it is an object of the present invention to provide a computer-implemented method for processing mass spectrometry data obtained from a breath gas, wherein the method enables the elimination of signals originating from contaminations, in particular transient contaminations.

According to the first aspect of the invention, a method for processing mass spectrometry data obtained from a breath gas is provided. The method comprises:

- receiving a time-dependent ion profile originating from a spectrometer data sample, the spectrometer data sample having been recorded during at least one exhalation from a human or animal subject; each time-dependent ion profile being associated with one mass-to-charge ratio value and comprising a signal strength for said one mass-to-charge ratio value measured over a time duration;
- receiving a time-dependent breath profile, the time-dependent breath profile having been recorded during said at least one exhalation over said time duration.

The method further comprises a temporal correlation step, the temporal correlation step comprising:

- determining a degree of temporal correlation between the time dependent ion profile and the time-dependent breath profile; and
- classifying the time-dependent ion profile based on the degree of temporal correlation as either a signal of interest or a signal not correlated with the exhalation of the subject.

Preferably, the time-dependent breath profile is a capnogram, i.e. a data set comprising the concentration (e.g., expressed as a percentage or expressed as mass per volume) or the partial pressure of carbon dioxide ($CO_2$) in the breath gas as a function of time, the capnogram having been measured simultaneously with the spectrometer data sample. The capnogram may be recorded by directing a portion of the breath gas into a capnograph comprising a sensor configured to measure the concentration or the partial pressure of $CO_2$, while another portion of the breath gas is simultaneously analyzed in a mass spectrometer to yield the spectrometer data sample.

Alternatively, the time-dependent breath profile may be a time-dependent total ion profile derived from the spectrometer data sample. In order to obtain such a time-dependent total ion profile, a range of mass-to-charge ratio values may be defined, the range preferably covering the mass-to-charge ratio values of a plurality of compounds that may be of interest to a user, and a sum of the signal strengths of all mass-to-charge ratio values falling into said range may be computed for each measurement point in time.

As another alternative, the time-dependent breath profile may be a time-dependent ion profile of a compound that is known to be present in the breath gas of the human or animal subject during the at least one exhalation, but which is either absent or only occurs in very small quantities in background air, such as proline, glutamine, lactic acid and other compounds. Alternatively, a substance being known to cause a specific compound to be present in the breath gas during the time over which the measurements are performed may be administered to the subject prior to the measurements.

The degree of temporal correlation may be expressed as a correlation coefficient for each time-dependent ion profile.

The correlation coefficient may be Pearson's linear correlation coefficient $\rho_{pearson}$. For a column $A_a$ in a matrix A and a column $B_b$ in a matrix B having means $$\overline{A_a} = \Sigma_{i=1}^{n}(A_{a,i})/n \text{ and}$$

$$\overline{B_b} = \Sigma_{i=1}^{n}(B_{b,i})/n$$

(where $A_{a,i}$ and $B_{b,i}$ are the matrix elements in the respective column and n is the total number of elements in the column), Pearson's linear correlation coefficient $\rho_{pearson}$ is defined as $$\rho_{pearson}(A_a, B_b) = \frac{\sum_{i=1}^{n}\left(A_{a,i} - \overline{A_a}\right)\left(B_{b,i} - \overline{B_b}\right)}{\left\{\sum_{i=1}^{n}\left(A_{a,i} - \overline{A_a}\right)^2 \sum_{i=1}^{n}\left(B_{b,i} - \overline{B_b}\right)^2\right\}^{1/2}}.$$

Preferably however, the degree of temporal correlation is determined by computing Spearman's rank correlation coefficient, which is equivalent to Pearson's linear correlation coefficient applied to the rankings (rank variables) of the elements in the columns $A_a$ and $B_b$. If all rank variables are distinct integers, Spearman's rank correlation coefficient simplifies to $$\rho_{spearman}(A_a, B_b) = 1 - \frac{6\sum_{i=1}^{n} d_i^2}{n(n^2 - 1)},$$

where $d_i$ is the difference between the rank variables of the matrix elements in the two columns for index i, i.e. $d_i = rg(A_{a,i}) - rg(B_{b,i})$. In practice, Spearman's rank correlation coefficient has shown to yield more robust results than Pearson's linear correlation coefficient when determining the degree of temporal correlation between a time-dependent ion profile and a time-dependent breath profile.

In order to separate signals of interest from signals that are not correlated with the exhalation of the subject, classifying the at least one time-dependent ion profile may comprise:

selecting the time-dependent ion profile if its correlation coefficient is higher than or equal to a pre-determined correlation threshold, and/or discarding the time-dependent ion profile if its correlation coefficient is lower than the pre-determined correlation threshold.

To enhance the robustness of the classifying step, the temporal correlation step may further comprise computing a p-value associated with each correlation coefficient (for testing the hypothesis of no correlation against the alternative hypothesis of a nonzero correlation) and computing a false discovery rate associated with each p-value. A selected time-dependent ion profile (i.e. a time-dependent ion profile whose correlation coefficient is higher than or equal to a pre-determined correlation threshold) may still be discarded if the false discovery rate is higher than a pre-determined false discovery rate threshold. Computing the false discovery rate may comprise a linear step-up procedure as introduced by Y. Benjamini and Y. Hochberg, "Controlling the false discovery rate: A practical and powerful approach to multiple testing", J. Royal Stat. Soc. 57, 289-300 (1995), DOI: 10.1111/j.2517-6161.1995.tb02031.x.

The method may further comprise an integration step, the integration step comprising integrating each selected time-dependent ion profile over an integration time to obtain an integrated signal strength, and a normalization step, the normalization step comprising normalizing each integrated signal strength by said integration time to obtain a normalized signal strength. The integration time may be the same as the (total) time duration of the time-dependent ion profile, but may also be shorter depending on the medical question to be answered. In some cases, one may for instance be interested in only analyzing the compounds in a portion of the exhalation, such as its beginning or end phase and hence one may choose an integration time that is shorter than the total time duration of the time-dependent ion profile.

The method may be repeated for multiple time-dependent ion profiles associated with different mass-to-charge ratio values, each of said time-dependent ion profiles originating from the same spectrometer data sample. A feature list may be created comprising the selected mass-to-charge ratio values and their associated normalized signal strengths for said spectrometer data sample.

The feature list may be added to a final data matrix, the final data matrix comprising multiple feature lists originating from multiple spectrometer data samples. Specifically, the multiple spectrometer data samples may have been obtained from the breath gas of the same subject at different times, e.g., during different medical examinations. The final data matrix may then serve as a basis for further analysis depending on the scientific or medical question to be answered.

The final data matrix may be subjected to a pattern recognition algorithm to identify patterns in the final data matrix that are associated with a specific medical condition. In general, the larger the number of spectrometer data samples, the easier it may become for the algorithm to reliably recognize patterns in the final data matrix, and the easier it may become for scientific or medical personnel to link these patterns to the specific medical condition. Hence, the method preferably further comprises:

receiving a plurality of additional time-dependent ion profiles originating from at least one additional spectrometer data sample, the at least one additional spectrometer data sample having been recorded during at least one exhalation from the subject; each additional time-dependent ion profile being associated with one mass-to-charge ratio value and comprising a signal strength for said one mass-to-charge ratio value measured over a time duration;

receiving a time-dependent breath profile associated with each additional spectrometer data sample, the associated time-dependent breath profile having been recorded during said at least one exhalation over said time duration;

repeating the temporal correlation step for each additional time-dependent ion profile;

establishing an additional feature list of the mass-to-charge ratio values and their normalized signal strengths for each additional spectrometer data sample, and a filtering step, the filtering step comprising filtering the feature lists by discarding each mass-to-charge ratio value which is present in less than a pre-determined percentage of the feature lists.

The filtering step increases the probability that only entries associated with "significant" compounds are present in the final data matrix. A compound is considered "significant" if it is consistently present in a subject's breath gas across multiple spectrometer data samples. The filtering step thus may help to eliminate signals associated with compounds that may be temporally correlated with exhalations, but may not be clinically or scientifically relevant, as they only occur in a few measurements and may be the result of special circumstances that are not relevant for answering a user's scientific or medical question. One example would be metabolites of a painkiller like paracetamol, which might be present in a subject's breath only in some data samples which were obtained at times when the subject had ingested paracetamol. Such metabolites might not be relevant in a study that is unrelated to paracetamol ingestion.

The method may further comprise a spectral feature extraction step to obtain the time-dependent ion profile from a spectrometer data sample. The spectral feature extraction step aims at determining which mass-to-charge ratio values actually belong to the same ion, even in the presence of instrumental drifts within the mass spectrometer over time, which may cause the mass spectrometer to output spectral data that shows slightly different mass-to-charge ratio values for the same ion at different points in time.

The spectral feature extraction step may comprise:

receiving at least one spectrometer data sample;

extracting a plurality of spectral scan arrays from the at least one spectrometer data sample, each spectral scan array being associated with a different point in time and consisting of mass-to-charge ratio values for which the signal strength is non-zero;

pooling all mass-to-charge ratio values from all spectral scan arrays into one mass-to-charge ratio pool;

partitioning the mass-to-charge ratio pool into bins with pre-determined equidistant bin centers and a pre-determined bin width;

determining a kernel density estimate function based on all mass-to-charge ratio values and evaluating the kernel density estimate function at each bin center;

extracting the bin centers for which the evaluated kernel density estimate function is larger than a pre-determined bin-count threshold;

establishing a peak list with peak list elements, the peak list elements corresponding to the extracted bin centers, and extracting from the at least one spectrometer data sample a time-dependent ion profile for each peak list element.

The spectrometer data sample preferably consists of centroid data, i.e. it consists only of mass-to-charge ratio values for which the signal strength is non-zero. Most commercial mass spectrometer directly enable the output of centroid data. Alternatively, the spectrometer data sample may also consist of profile data or another type of raw data. In such a case, the step of extracting a plurality of spectral scan arrays from the at least one spectrometer data sample may comprise converting non-centroid data to centroid data via a peak-search function or any other suitable function.

In general, the kernel density estimate function is given by $$f_k(x) = \frac{1}{Nh}\sum_{i=1}^{N} K\left(\frac{x - x_i}{h}\right),$$

where $x_i$ are random samples from an unknown distribution, N is the number of samples, h is the bandwidth and K is the kernel smoothing function. Here, the mass-to-charge values in the pool represent the random samples and the bin centers are the points at which the kernel density estimate function $f_k$ is evaluated. The kernel smoothing function may be one of the commonly used smoothing functions such as Gaussian, uniform (rectangular window), triangle, Epanechikov or any other suitable function.

Extracting the time-dependent ion profile for each peak list element may further comprise:

determining a peak width of the kernel density estimate function evaluated at each peak-list element;

computing an average signal strength for each peak-list element by averaging the signal strengths of all mass-to-charge ratio values that lie within an interval defined by the peak width around the peak-list elements in each scan array, and creating a time-dependent ion profile for each peak-list element by attributing the average signal strength of each peak-list element from each spectral scan array to the point in time that is associated with said spectral scan array.

The peak width may for instance be defined as the full width at half maximum (FWHM) of the kernel density estimate function evaluated at each peak-list element.

In order to optimize the choice of bandwidth for the kernel density estimate function, the method may further comprise:

receiving a mass-spectrometer-specific instrument parameter;

determining a peak width of the kernel density estimate function evaluated at a peak-list element;

setting an initial bandwidth for the kernel density estimate function;

comparing the peak width with the mass-spectrometer-specific instrument parameter evaluated at a peak-list element, and iteratively adjusting the initial bandwidth for the kernel density estimate function until the peak width lies within a pre-determined interval around the massspectrometer-specific specific instrument parameter evaluated at said peak-list element.

The mass-spectrometer-specific instrument parameter may be a mass-spectrometer resolution function. Alternatively, the mass-spectrometer-specific instrument parameter may also be a relative instrument error function, such as e.g. the expected mass accuracy, or any other suitable parameter.

In a second aspect, the present invention provides a computer program product comprising instructions which, when the program is executed by a computer, cause the computer to carry out the method according to the first aspect of the invention.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1A:
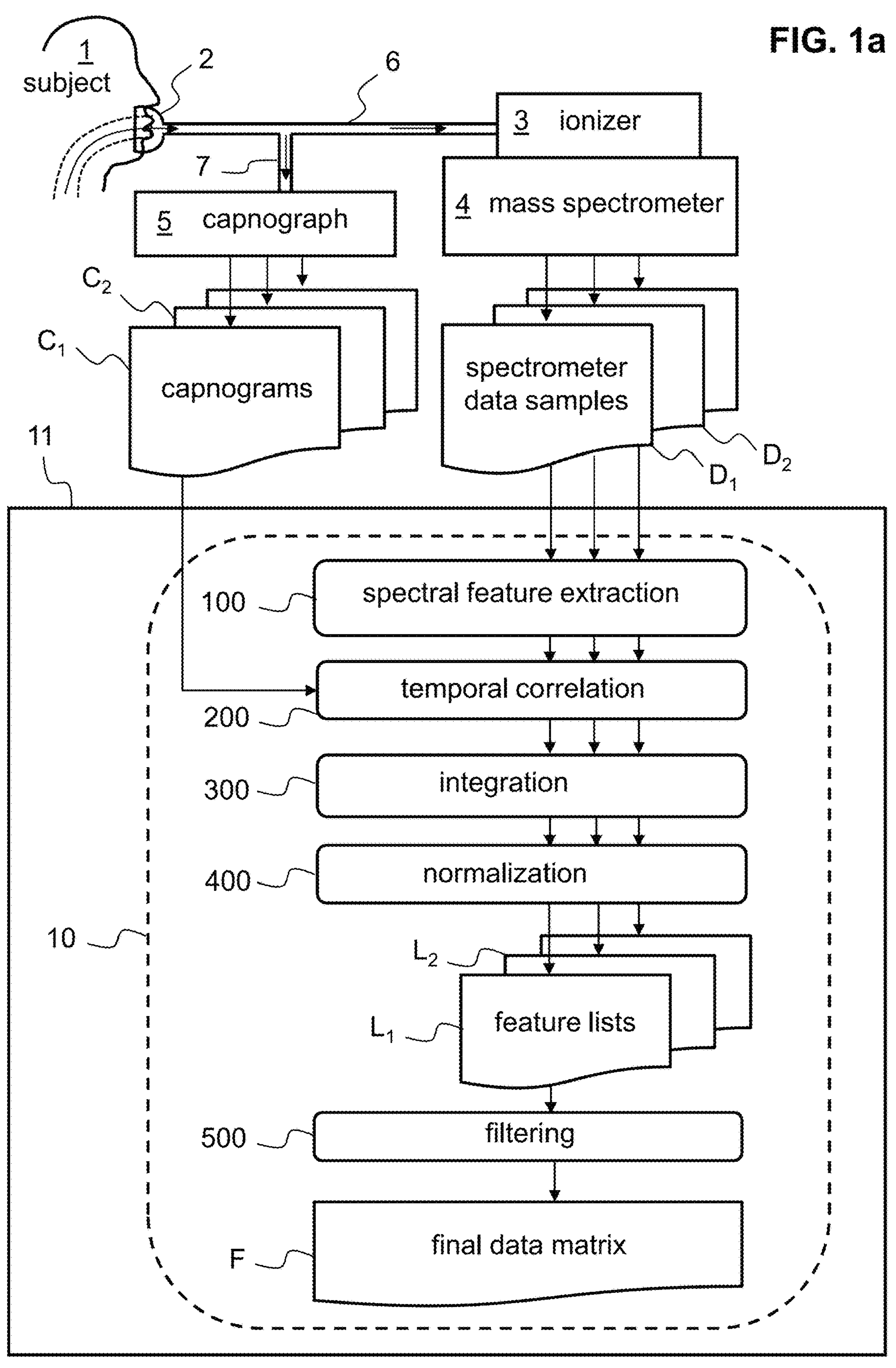
FIG. 1*a* shows, in a schematic manner, a computer-implemented method for processing mass spectrometry data obtained from breath gas according to a first embodiment of the present invention.

FIG. 1*a* illustrates, in a schematic manner, a computer-implemented method for processing mass spectrometry data obtained from breath gas according to a first embodiment of the present invention. A subject 1 exhales through a mouthpiece 2, the mouthpiece 2 being attached to a main tubing arrangement 6, the main tubing being configured to guide the subject's exhaled breath gas into an ionizer 3 which is connected to a mass spectrometer 4. The mass spectrometer 4 outputs data in the form of spectrometer data samples $D_1$,$D_2$. Ideally, the spectrometer data samples $D_1$,$D_2$ comprise already centroid data. The spectrometer data samples $D_1$,$D_2$ are read into a computer 11 by a computer program product 10. The computer program then executes the following steps: feature extraction 100, temporal correlation 200, integration 300, normalization 400, creating feature lists $L_1$,$L_2$, filtering 500 the feature lists $L_1$,$L_2$, and creating a final data matrix F. In this first embodiment, an auxiliary tubing arrangement 7 directs a portion of the exhaled breath gas into a capnograph, which is configured to be operated in parallel to the mass spectrometer and which output capnograms $C_1$,$C_2$. The capnograms $C_1$,$C_2$ are read into the computer 11 and are used in the temporal correlation step 200.

Figure 1B:
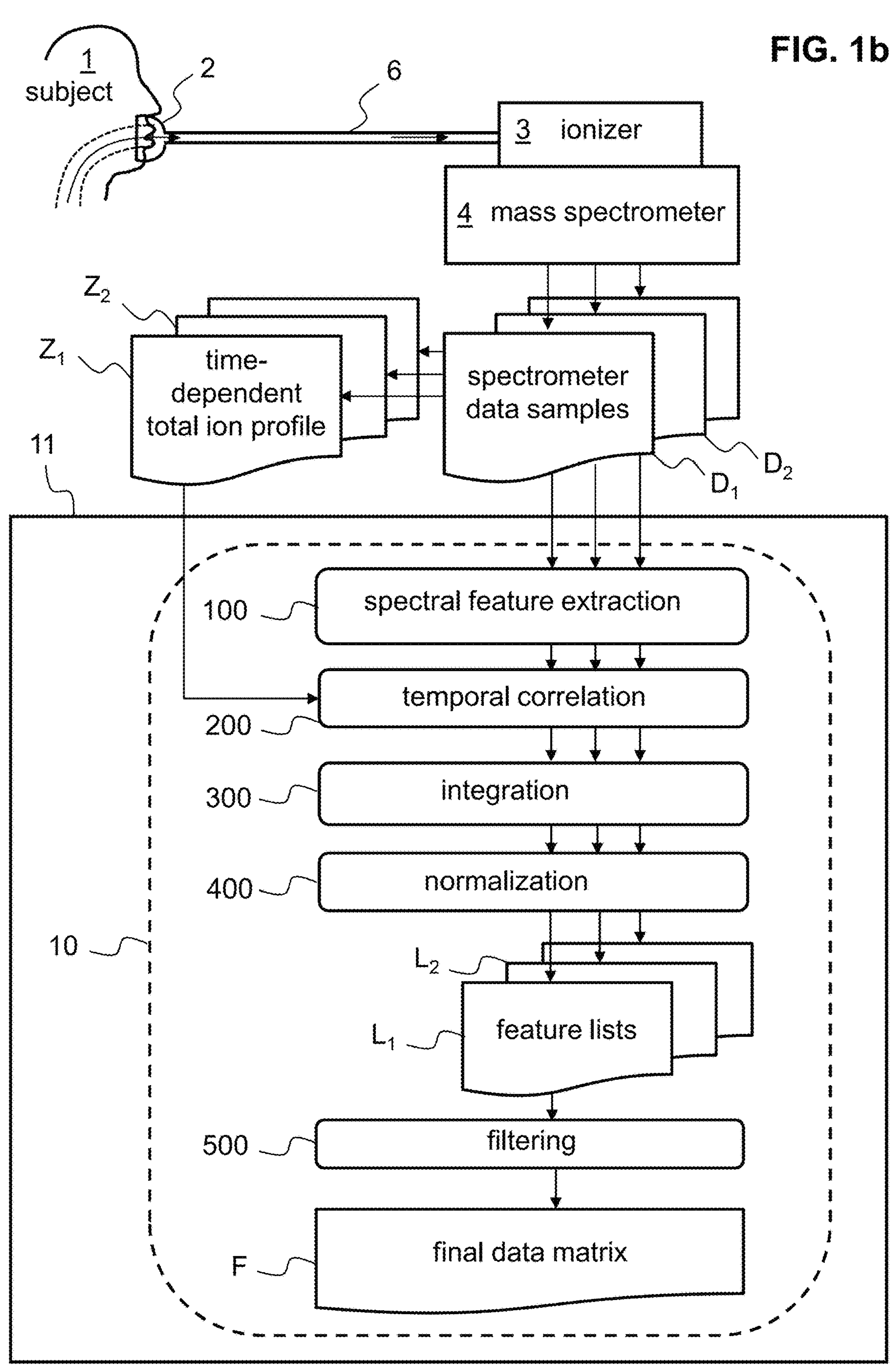
FIG. 1*b* shows, in a schematic manner, a computer-implemented method for processing mass spectrometry data obtained from breath gas according to a second embodiment of the present invention.

FIG. 1*b* illustrates, in a schematic manner, a computer-implemented method for processing mass spectrometry data obtained from breath gas according to a second embodiment. This second embodiment differs from the first embodiment depicted in FIG. 1*a* in that time-dependent total ion profiles $Z_1$,$Z_2$ are extracted from the spectrometer data samples $D_1$,$D_2$ and used in the temporal correlation step 200 instead of the capnograms $C_1$,$C_2$.

Figure 2:
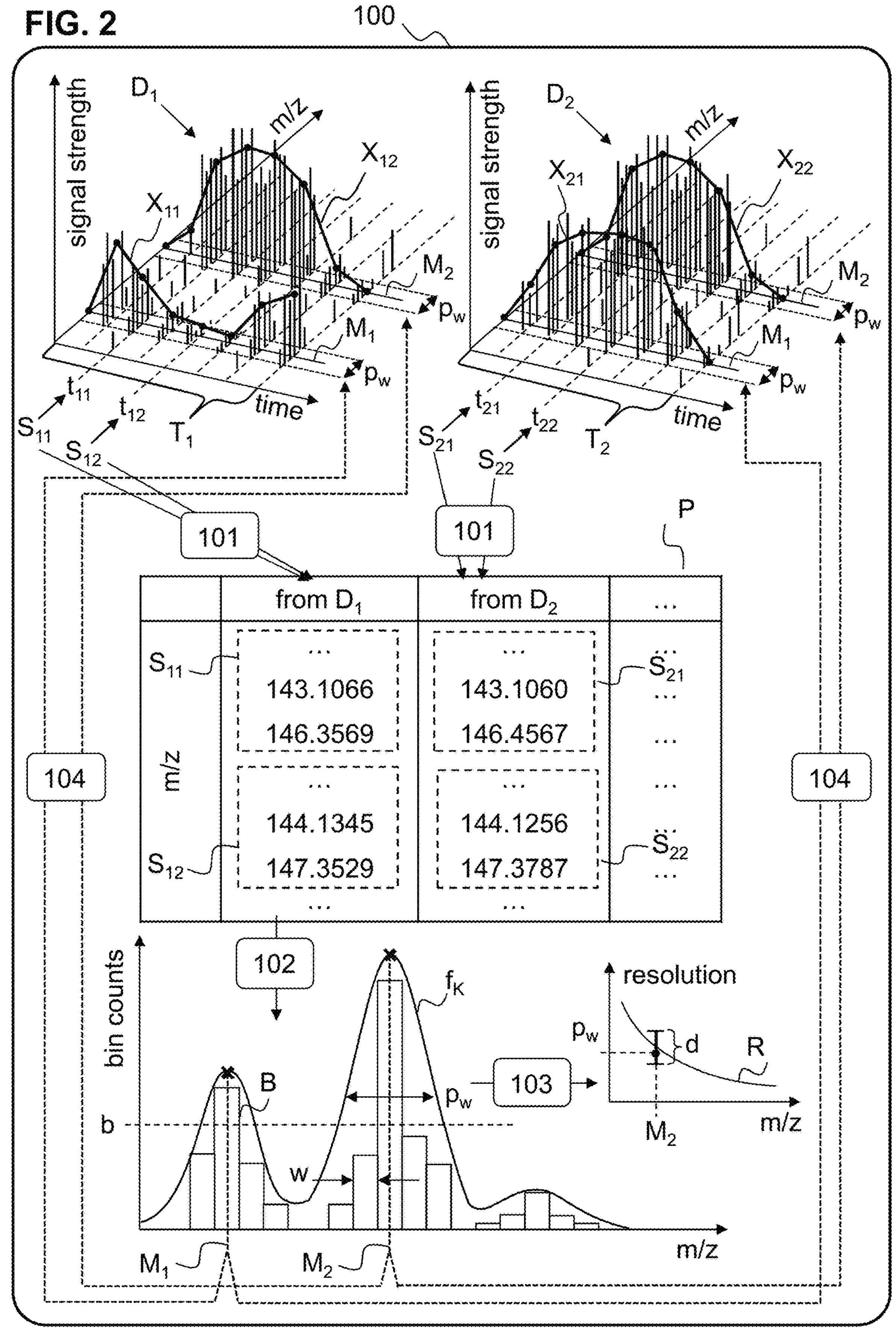
FIG. 2 schematically illustrates a feature extraction step.

FIG. 2 schematically illustrates the feature extraction step 100. Note that the following nomenclature is used for reference signs with two-digit indices: the first digit represents the spectrometer data sample (i.e. $D_1$ or $D_2$) with which the object, to which the reference sign refers, is associated, while the second digit is used for numbering the objects belonging to the same spectrometer data sample. The spectrometer data samples $D_1$,$D_2$ comprise signal strengths for a range of mass-to-charge ratio values measured at different points in time $t_{11}$,$t_{12}$,$t_{21}$,$t_{22}$ within a time duration $T_1$,$T_2$. Typical time durations $T_1$,$T_2$ are on the order of 100-200 seconds, which generally corresponds to 5-6 consecutive exhalations which each have a typical duration of 15 s and are followed by a break of typically 10 seconds (only one exhalation is schematically shown in FIG. 2). In the specific embodiment of the method shown in FIG. 2, the spectrometer data samples consists of centroid data, i.e. the spectrometer data samples consists only of mass-to-charge ratio values for which the signal strength is non-zero. A plurality of spectral scan arrays $S_{11}$,$S_{12}$,$S_{21}$,$S_{22}$ (typically 10-20 per exhalation) are extracted from the spectrometer data samples $D_1$,$D_2$, each spectral scan array $S_{11}$,$S_{12}$,$S_{21}$,$S_{22}$ being associated to a different point in time $t_{11}$,$t_{12}$,$t_{21}$,$t_{22}$.

In a pooling step 101, all mass-to-charge ratio values from all spectral scan arrays are pooled into one mass-to-charge ratio pool P. The mass-to-charge ratio pool P is then partitioned 102 into bins B with pre-determined equidistant bin centers and a pre-determined bin width w. The bin counts schematically shown in FIG. 2 represent the number of mass-to-charge ratio values in each bin B.

A kernel density estimate function $f_K$ is determined based on all mass-to-charge ratio values and the kernel density estimate function $f_K$ is evaluated at each bin center. In order to find an optimum bandwidth for the kernel density estimate function $f_K$, an initial bandwidth h is first set for the kernel density estimate function.

Subsequently, a peak width $p_w$ of the kernel density estimate function $f_K$ evaluated at a peak-list element $M_2$ is determined and compared 103 with a mass-spectrometer-specific instrument parameter, in this specific case the resolution function R of the mass spectrometer evaluated at a peak-list element $M_2$. Then, the initial bandwidth h for the kernel density estimate function $f_K$ is iteratively adjusted until the peak width $p_w$ lies within a pre-determined interval d around the mass-spectrometer-specific instrument parameter, in this case the resolution function R evaluated at said peak-list element $M_2$.

Once the optimum bandwidth for the kernel density estimate function $f_K$ has been found, the bin centers for which the evaluated kernel density estimate function $f_K$ is larger than a pre-determined bin-count threshold b are extracted. A peak list with peak list elements $M_1$, $M_2$ is established, the peak list elements $M_1$,$M_2$ corresponding to the extracted bin centers. Once the peak list has been established, a time-dependent ion profile $X_{11}$, $X_{12}$,$X_{21}$, $X_{22}$ is extracted 104 for each peak list element $M_1$, $M_2$ from each data sample $D_1$,$D_2$.

Figures 3A, 3B:
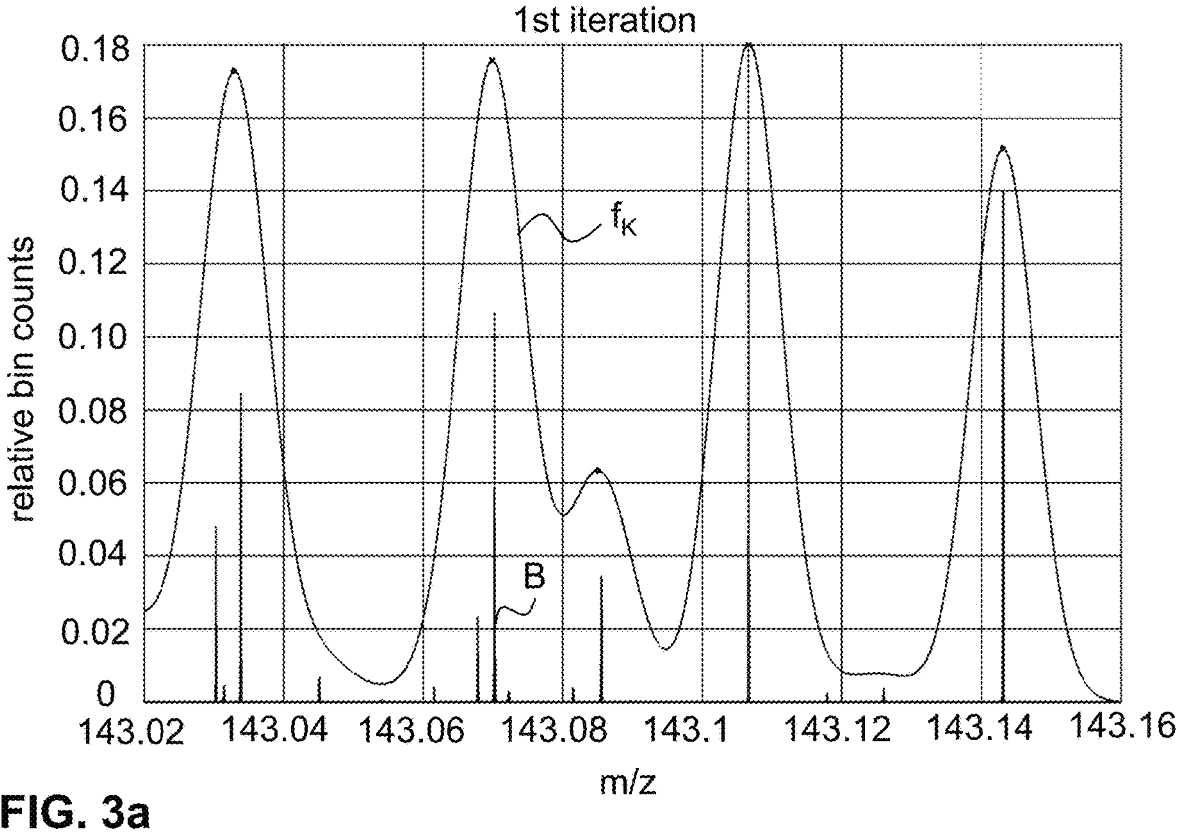
FIG. 3*a-b* show real experimental data together with a kernel density estimate function at different iterations of a bandwidth-optimization process.

In FIGS. 3*a* and 3*b*, relative bin counts originating from real experimental data are depicted together with the kernel density estimate function $f_k$ at different iterations of the bandwidth-optimization process 103. The relative bin counts are obtained by dividing the bin counts by the total number of spectral scan arrays that were used to create the mass-to-charge ratio pool P. FIG. 3*a* shows the first iteration, i.e. where the bandwidth of the kernel density estimate function $f_k$ is not yet appropriate as it leads to a peak width $p_w$ that is too large, while FIG. 3*b* shows the $14^{th}$ iteration, where the bandwidth of the kernel density estimate function $f_k$ has been optimized.

Figure 4:
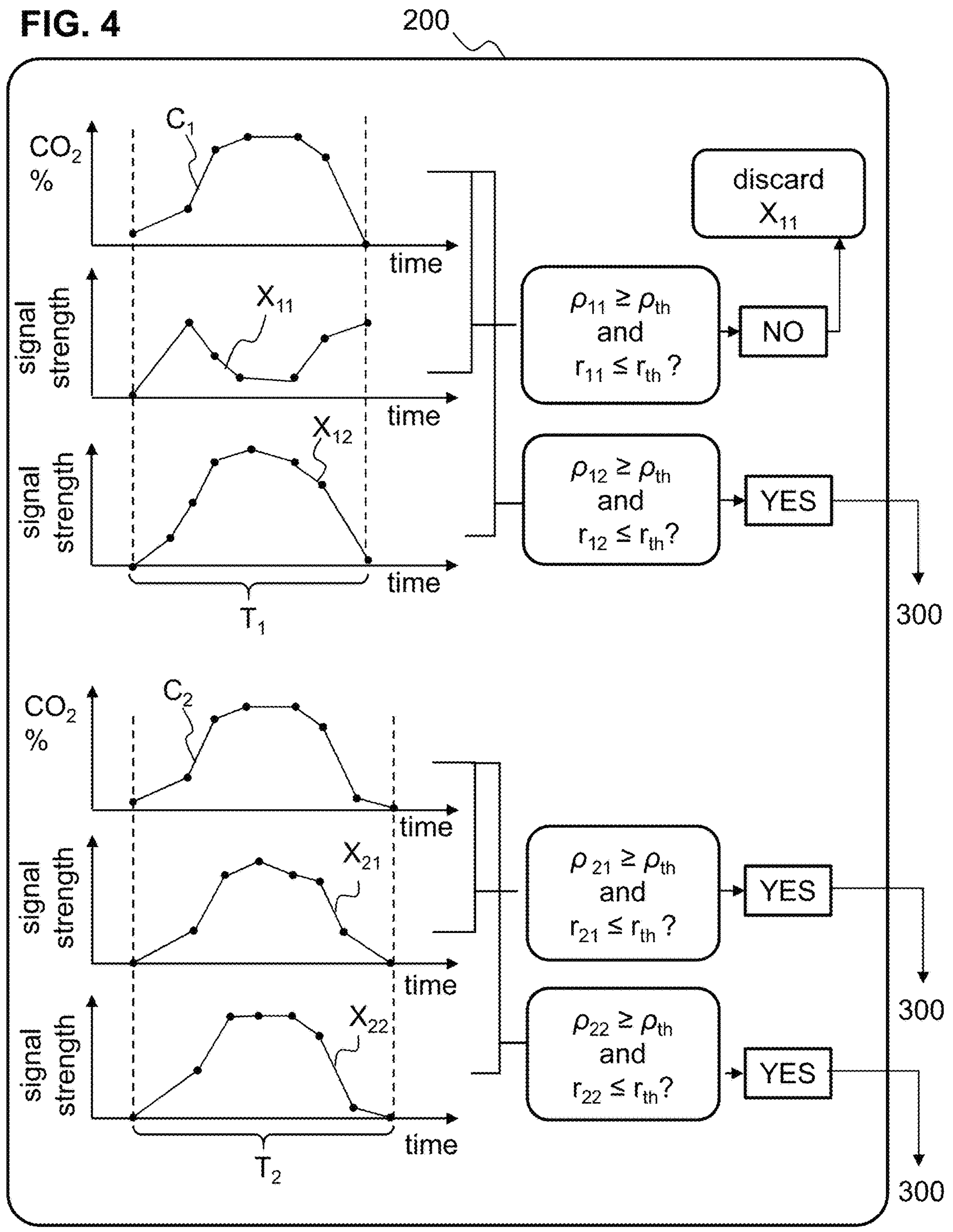
FIG. 4 schematically illustrates a temporal correlation step according to a preferred embodiment using capnograms as time-dependent breath profiles.

FIG. 4 schematically illustrates the temporal correlation step 200 according to a preferred embodiment using capnograms $C_1$,$C_2$ as time-dependent breath profiles. A correlation coefficient $\rho_{11}$,$\rho_{12}$,$\rho_{21}$,$\rho_{22}$, a p-value associated with each correlation coefficient $\rho_{11}$,$\rho_{12}$,$\rho_{21}$,$\rho_{22}$ and a false discovery rate $r_{11}$,$r_{12}$,$r_{21}$,$r_{22}$ is computed for each time-dependent ion profile $X_{11}$,$X_{12}$,$X_{21}$,$X_{22}$. In the example illustrated in FIG. 4, the time-dependent ion profiles $X_{12}$,$X_{21}$,$X_{22}$ are selected for further processing, since their correlation coefficients $\rho_{12}$,$\rho_{21}$,$\rho_{22}$ are each higher than or equal to a pre-determined correlation threshold $\rho_{th}$, while their associated false discovery rates $r_{12}$,$r_{21}$,$r_{22}$ are each lower than or equal to a pre-determined false discovery rate threshold $r_{th}$. On the other hand, the time-dependent ion profile $X_{11}$ is discarded. In practice, satisfactory results may be obtained by using Spearman's rank correlation coefficient and setting the correlation threshold to $\rho_{th}$=0.7 and the false discovery rate threshold to $r_{th}$=0.01.

Figure 5A:
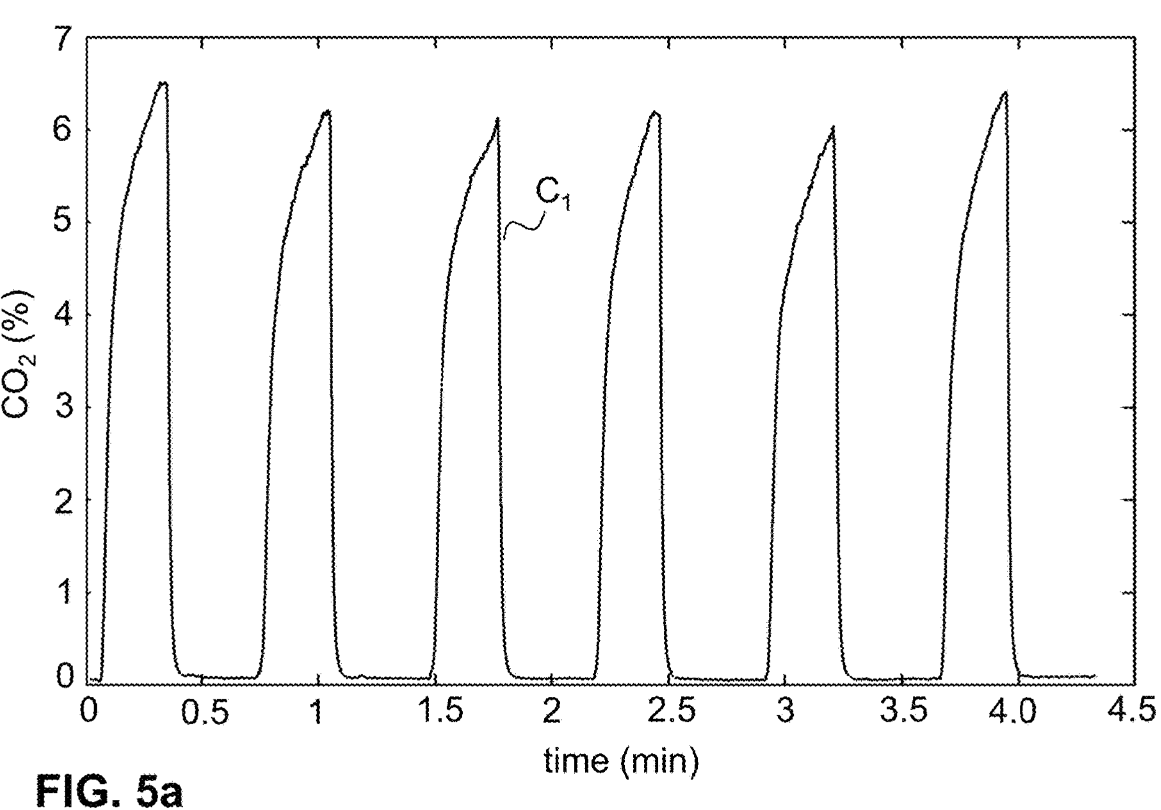
FIG. 5*a* shows a capnogram obtained in a real measurement.

FIG. 5*a* shows a capnogram $C_1$ of six consecutive exhalations obtained in a real measurement, the capnogram $C_1$ indicating the percentage of $CO_2$ as a function of time.

Figure 5B:
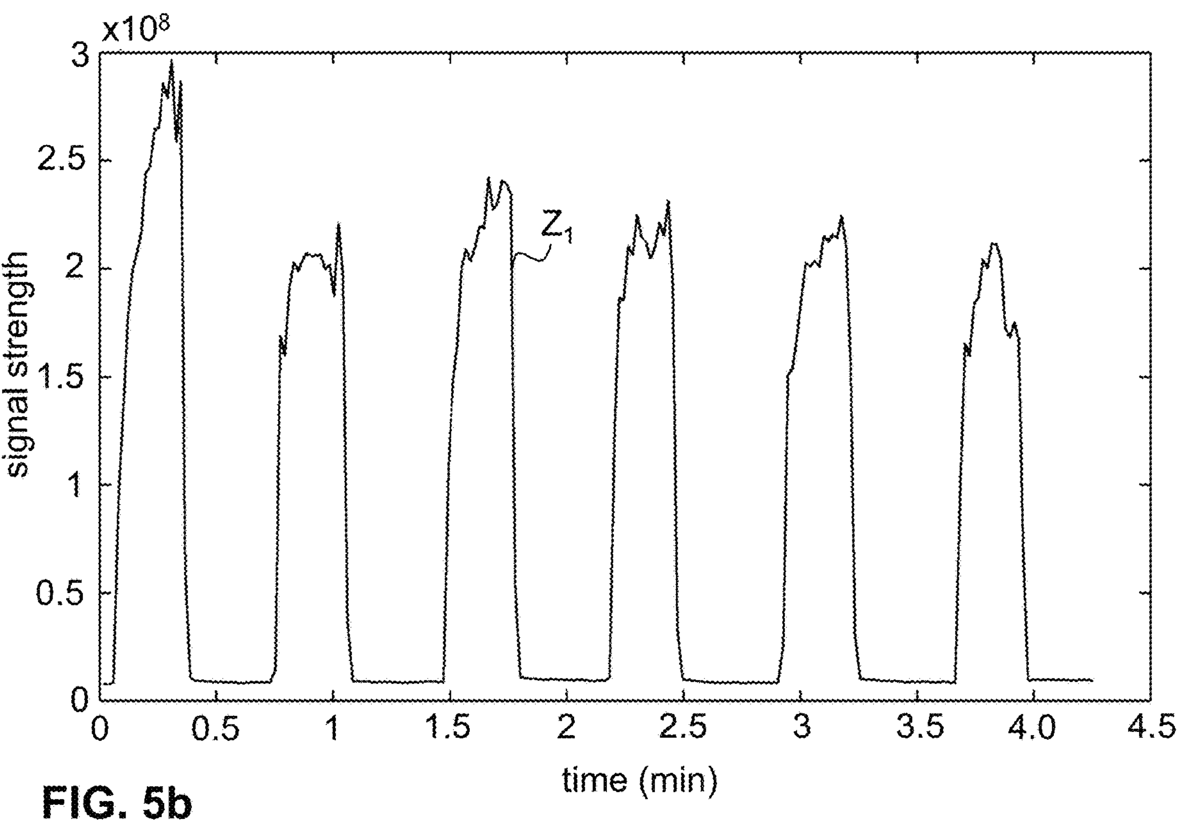
FIG. 5*b* shows a time-dependent total ion profile obtained in a real measurement.

FIG. 5*b* shows a time-dependent total ion profile $Z_1$ obtained simultaneously to the capnogram $C_1$ shown in FIG. 5*a* during the same six consecutive exhalations, the time-dependent total ion profile $Z_1$ indicating the signal strength in arbitrary units of all detected ions combined as a function of time.

Figure 5C:
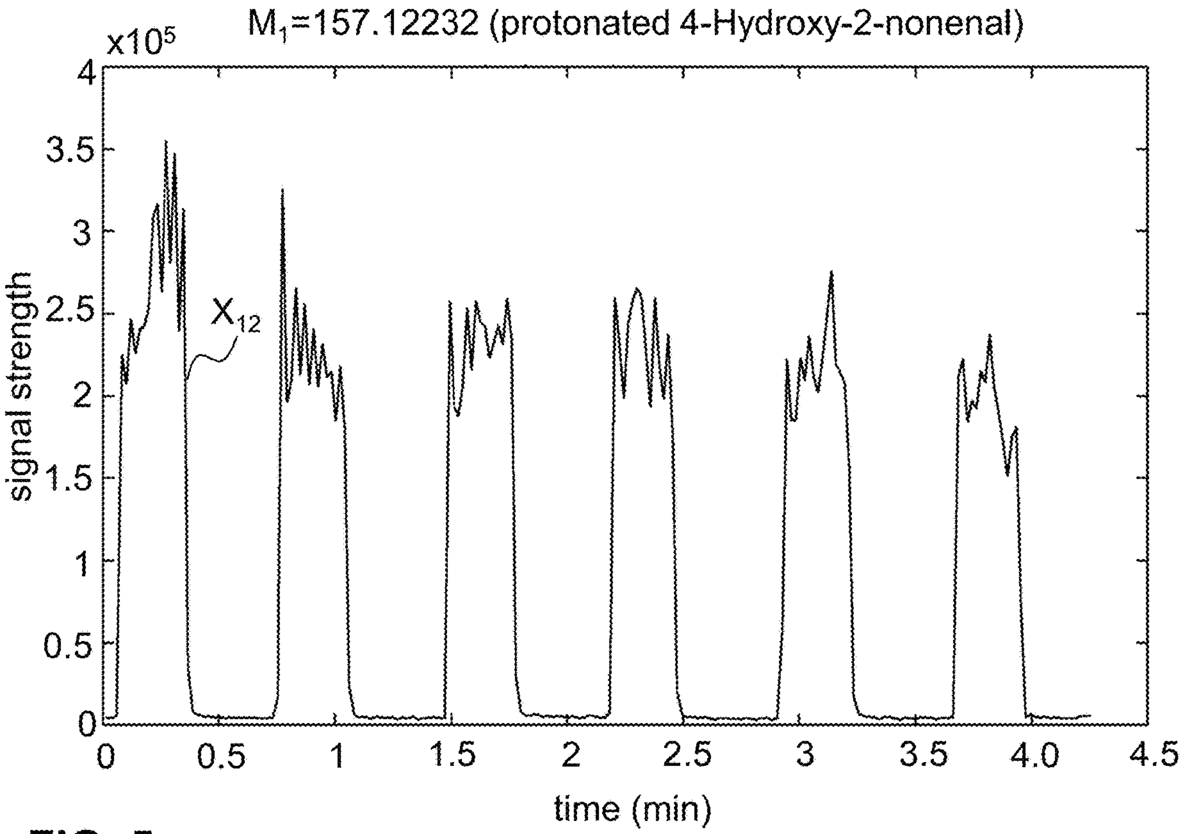
FIG. 5*c* shows a time-dependent ion profile obtained in a real measurement.

FIG. 5*c* shows a time-dependent ion profile $X_{12}$ obtained simultaneously to the capnogram $C_1$ shown in FIG. 5*a* for a mass-to-charge ration value of $M_1$=157.12232, which corresponds to protonated 4-Hydroxy-2-nonenal.

A simple visual comparison of this time-dependent ion profile $X_{12}$ with the time-dependent total ion profile $Z_1$ shown in FIG. 5*b* and/or the capnogram $C_1$ shown in FIG. 5*a* already indicates a high degree of temporal correlation, which in turn indicates that protonated 4-Hydroxy-2-nonenal has a high probability of being a metabolite of interest and not a contamination.

Figure 6:
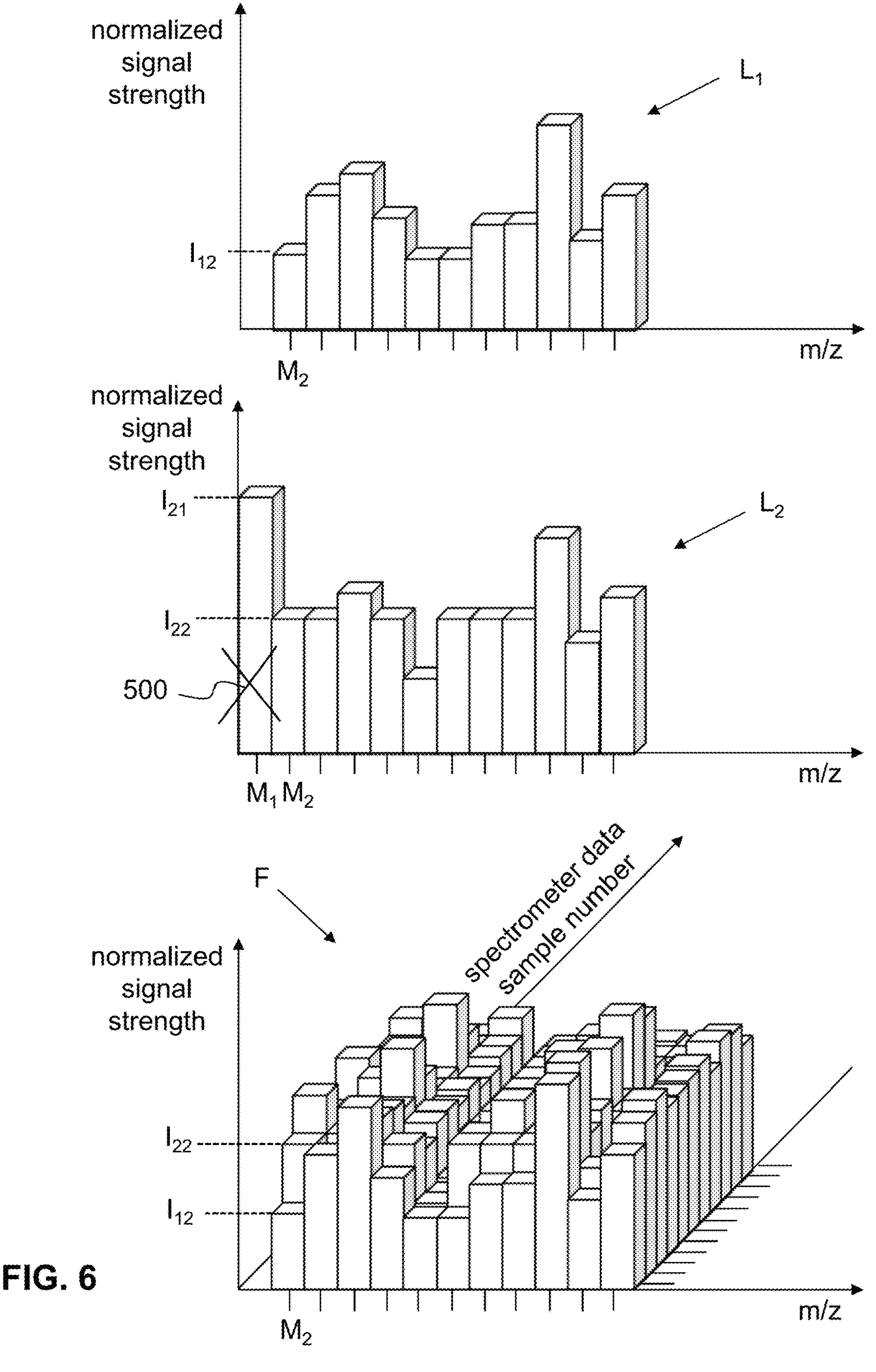
FIG. 6 shows, in a schematic manner, a filtering step and the creation of a final data matrix.

In FIG. 6, the filtering step 500 and the creation of a final data matrix F are schematically depicted. Features lists $L_1$,$L_2$ of the mass-to-charge ratio values $M_1$, $M_2$ and their normalized signal strengths $I_{11}$,$I_{21}$,$I_{22}$ are established for each spectrometer data sample $D_1$,$D_2$. The feature lists are $L_1$,$L_2$ are filtered 500 before being added to the final data matrix F: each mass-to-charge ratio value $M_1$ which is present in less than a pre-determined percentage of the feature lists $L_1$,$L_2$ is discarded. In this graphic example, the predetermined percentage is set to 100% for illustrative purposes, hence, the mass-to-charge ratio value $M_1$, which is only present in the list $L_2$, is discarded. In practice, satisfactory results may be obtained by setting the predetermined percentage to a value in the range of 75% to 85%. If a measurement series contains spectrometer data samples that originate from control measurements, the predetermined percentage may be reduced to approximately the ratio of case samples to control samples.

The invention claimed is:

1. A computer-implemented method for processing mass spectrometry data obtained from a breath gas, the method comprising:

receiving a time-dependent ion profile originating from a spectrometer data sample, the spectrometer data sample having been recorded during at least one exhalation from a human or animal subject; the time-dependent ion profile being associated with one mass-to-charge ratio value and comprising a signal strength for said one mass-to-charge ratio value measured over a time duration;

receiving a time-dependent breath profile, the time-dependent breath profile having been recorded during said at least one exhalation over said time duration;

wherein the method comprises a temporal correlation step, the temporal correlation step comprising:

determining a degree of temporal correlation between the time-dependent ion profile and the time-dependent breath profile, and classifying the time-dependent ion profile based on the degree of temporal correlation as either a signal of interest originating from the exhalation of the subject or a signal not correlated with the exhalation of the subject.

2. The method of claim 1, wherein the time-dependent breath profile is a time-dependent total ion profile derived from the spectrometer data sample.

3. The method of claim 1, wherein the time-dependent breath profile is a capnogram, the capnogram having been measured simultaneously with the spectrometer data sample.

4. The method of claim 1, wherein the time-dependent breath profile is a time-dependent ion profile of proline, glutamine or lactic acid, or a compound originating from a substance that has been administered to the subject prior to recording the spectrometer data sample.

5. The method of claim 1, wherein the degree of temporal correlation is expressed as a correlation coefficient for the time-dependent ion profile, and wherein classifying the time-dependent ion profile comprises:

selecting the time-dependent ion profile if the correlation coefficient is higher than or equal to a pre-determined correlation threshold, or discarding the time-dependent ion profile if the correlation coefficient is lower than the pre-determined correlation threshold.

6. The method of claim 5, the temporal correlation step further comprising:

computing a p-value associated with each correlation coefficient;

computing a false discovery rate associated with each p-value, and discarding the selected time-dependent ion profile if the false discovery rate is higher than a pre-determined false discovery rate threshold.

7. The method of claim 5, wherein the correlation coefficient is Spearman's rank correlation coefficient.

8. The method of claim 5, further comprising:

an integration step, the integration step comprising integrating the selected time-dependent ion profile over an integration time to obtain an integrated signal strength;

a normalization step, the normalization step comprising normalizing each integrated signal strength by said integration time to obtain a normalized signal strength;

creating a feature list comprising the mass-to-charge ratio values and their associated normalized signal strengths for said spectrometer data sample, and adding the feature list to a final data matrix.

9. The method of claim 8, further comprising:

receiving a plurality of additional time-dependent ion profiles originating from at least one additional spectrometer data sample, the at least one additional spectrometer data sample having been recorded during at least one exhalation from the subject; each additional time-dependent ion profile being associated with one mass-to-charge ratio value and comprising a signal strength for said one mass-to-charge ratio value measured over a time duration;

receiving a time-dependent breath profile associated with each additional spectrometer data sample, the associated time-dependent breath profile having been recorded during said at least one exhalation over said time duration;

repeating the temporal correlation step for each additional time-dependent ion profile;

establishing an additional feature list of the mass-to-charge ratio values and their normalized signal strengths for each additional spectrometer data sample, and a filtering step, the filtering step comprising filtering the feature lists by discarding each mass-to-charge ratio value which is present in less than a pre-determined percentage of the feature lists.

10. The method of claim 1, further comprising a spectral feature extraction step, the spectral feature extraction step comprising:

receiving at least one spectrometer data sample;

extracting a plurality of spectral scan arrays from the at least one spectrometer data sample, each spectral scan array being associated with a different point in time and composed of mass-to-charge ratio values for which the signal strength is non-zero;

pooling all mass-to-charge ratio values from all spectral scan arrays into one mass-to-charge ratio pool;

partitioning the mass-to-charge ratio pool into bins with pre-determined equidistant bin centers and a pre-determined bin width;

determining a kernel density estimate function based on all mass-to-charge ratio values and evaluating the kernel density estimate function at each bin center;

extracting the bin centers for which the evaluated kernel density estimate function is larger than a pre-determined bin-count threshold;

establishing a peak list with peak list elements, the peak list elements corresponding to the extracted bin centers, and extracting from the at least one spectrometer data sample a corresponding time-dependent ion profile for each peak list element.

11. The method of claim 10, wherein extracting the time-dependent ion profile for each peak list element comprises:

determining a peak width of the kernel density estimate function evaluated at each peak-list element;

computing an average signal strength for each peak-list element by averaging the signal strengths of all mass-to-charge ratio values that lie within an interval defined by the peak width around the peak-list elements in each scan array, and creating the corresponding time-dependent ion profile for each peak-list element by attributing the average signal strength of each peak-list element from each spectral scan array to the point in time that is associated with said spectral scan array.

12. The method of claim 10, the method further comprising:

receiving a mass-spectrometer-specific instrument parameter;

determining a peak width of the kernel density estimate function evaluated at a peak-list element;

setting an initial bandwidth for the kernel density estimate function;

comparing the peak width with the mass-spectrometer-specific instrument parameter evaluated at a peak-list element, and iteratively adjusting the initial bandwidth for the kernel density estimate function until the peak width lies within a pre-determined interval around the mass-spectrometer-specific instrument parameter evaluated at said peak-list element.

13. The method of claim 12, wherein the mass-spectrometer-specific instrument parameter is a mass-spectrometer resolution function.

14. A computer program product comprising instructions which, when the program is executed by a computer, cause the computer to carry out the method of claim 1.

* * * * *